United States Patent [19]

Turner et al.

[11] Patent Number: 5,048,512

[45] **Date of Patent: * Sep. 17, 1991**

[54] GASTROSTOMY TUBE PROTECTOR AND HIDER

[76] Inventors: W. Richard Turner; Linda T. Turner, both of 1677 S. 1806 W., Heber City, Utah 84032

[ * ] Notice: The portion of the term of this patent subsequent to Nov. 17, 2003 has been disclaimed.

[21] Appl. No.: 723,919

[22] Filed: Apr. 16, 1985

[51] Int. Cl.[5] .............................................. A61B 19/00

[52] U.S. Cl. .......................... 128/876; 128/DIG. 26; 604/179; 604/345

[58] Field of Search ................................ 604/174-180, 604/332, 345; 128/DIG. 26, 132 R, 132 D, 133, 155, 876

[56] References Cited

U.S. PATENT DOCUMENTS

| | | | |
|---|---|---|---|
| 2,476,513 | 7/1949 | Scott | 604/345 |
| 2,612,895 | 10/1952 | Magee | 604/345 X |
| 4,221,215 | 9/1980 | Mandelbaum | 128/155 |
| 4,470,410 | 9/1984 | Elliott | 128/133 |

*Primary Examiner*—C. Fred Rosenbaum

[57] ABSTRACT

A surgically implanted gastrostomy tube through which the wearer receives part or all of his required nourishment is an unnatural, awkward, inconvenient and damage-vulnerable appendage added to the human body that is approximately 10" to 16" long and ¼" in diameter, is made of surgical rubber tubing, and protrudes and dangles from the stomach area of the wearer. This invention, the gastrostomy tube protector and hider, is a belt or girdle worn by a person with a gastrostomy tube, that incorporates a pocket with a method of closure in which said gastrostomy tube can be stored and protected.

2 Claims, 3 Drawing Sheets

GASTROSTOMY TUBE PROTECTOR AND HIDER

BACKGROUND OF THE INVENTION

1. Field of the Invention

This invention relates to durable medical equipment and, more particularly, to a system and method for hiding and providing protection for a surgically implanted gastrostomy tube.

2. The Prior Art

Occasionally it becomes necessary for people with eating or feeding disorders or difficulties to have surgically implanted directly into the stomach, a gastrostomy tube. The gastrostomy tube, through which the wearer receives part or all of his required daily nourishment is an unnatural, awkward, inconvenient and damage-vulnerable appendage added to the human body that is approximately 10" to 16" long and ¼" in diameter, made of surgical rubber tubing, and that protrudes and dangles from the stomach area of the wearer.

Heretofore, individuals with implanted gastrostomy tubes had no satisfactory way to protect and hide said tube. Said tube simply dangled loose and was subject to dirt and damage, and the wearer suffered from insecurity, self-consciousness, and the worry of possible pain and inconvenience in the event the tube were to snag on something or otherwise be pulled (possible completely out—an event with somewhat serious implications). With the tube tucked inside of clothing as was sometimes done, it was still susceptible to most of the above problems. It sometimes showed through clothing, and often worked its way out of an opening in the clothing. In the case of an infant wearing a diaper, it often worked its way down inside or adjacent to the diaper and was subject to contamination from that source.

SUMMARY AND OBJECTS OF THE INVENTION

It is an object of this invention to provide a place for an individual with an implanted gastrostomy tube to store said tube.

It is another object of this invention to protect said gastrostomy tube from damage, contamination, and accidental extraction.

In accordance with the foregoing objects, our invention consists of a belt or girdle worn about the waist with a hole in it through which the gastrostomy tube can protrude. The belt incorporates a pocket with a method of closure in which the tube can then be stored, hidden and protected.

Further objects and advantages of our invention will become apparent from a consideration of the drawings and ensuing description thereof.

DETAILED DESCRIPTION OF THE PREFERRED EMBODIMENTS

Figure 1:
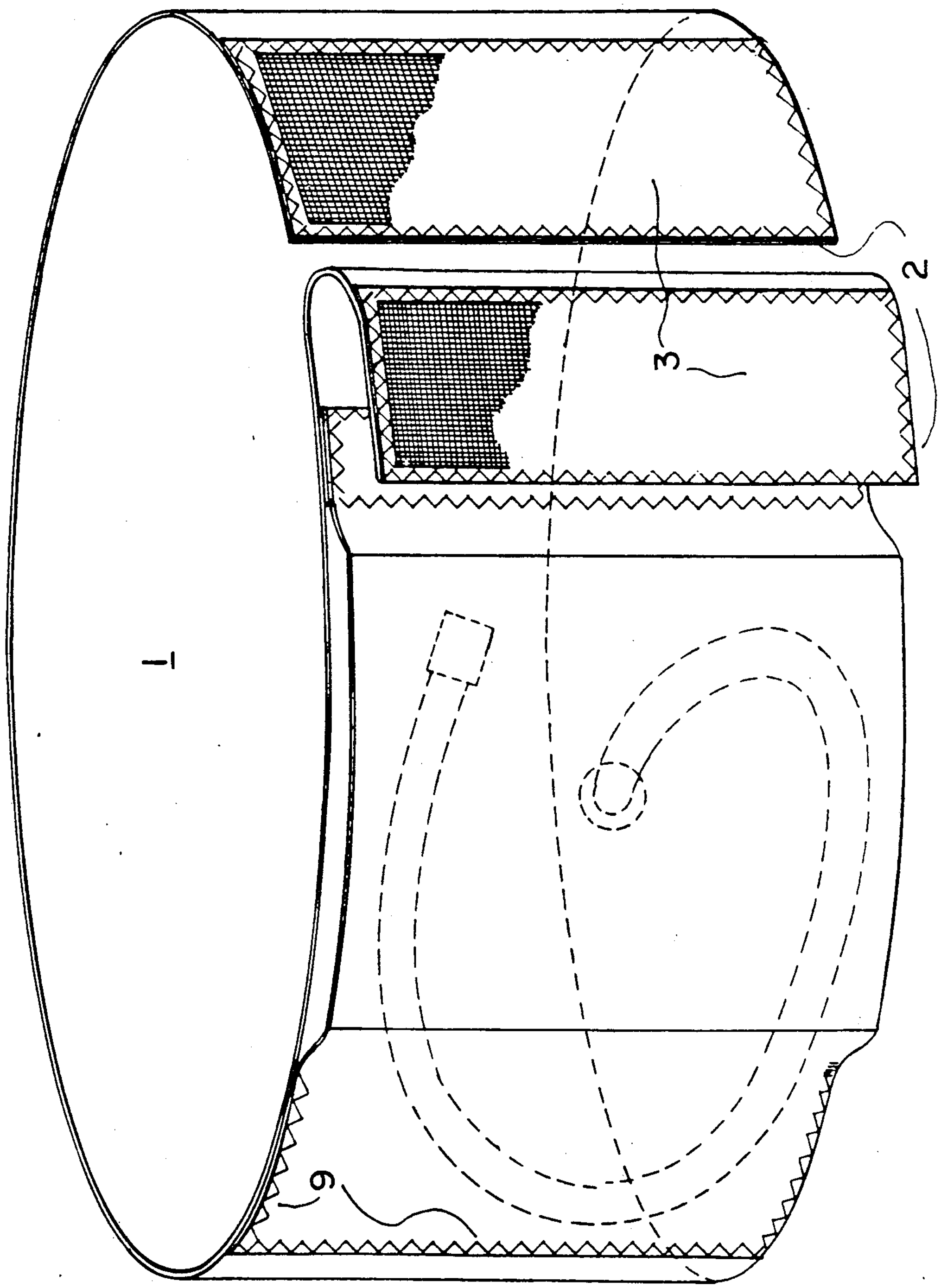
FIG. 1 shows the gastrostomy tube protector and hider with the loose ends in an unfastened mode.

Referring to FIG. 1 of the accompanying drawings, the gastrostomy tube protector and hider, also referred to herein as "the invention", is illustrated in its entirety. The invention's main body (1) in its preferred embodiment is a double layer of sturdy cotton-polyester fabric. It can begin as one large piece of fabric sewn into a tube, pressed flat, then sewn closed on the ends, or it can begin as two smaller pieces sewn together. At the two loose ends (2) are sewn strips of a fastening material (3) such as Velcro® in such a way that the loose ends (2) of the main body (1) can be fastened together securing the invention around the waist of the wearer. The strips of fastening material (3) are wide enough to provide a degree of adjustability for changes in waist size, depending upon how far said strips are overlapped.

Figure 2:
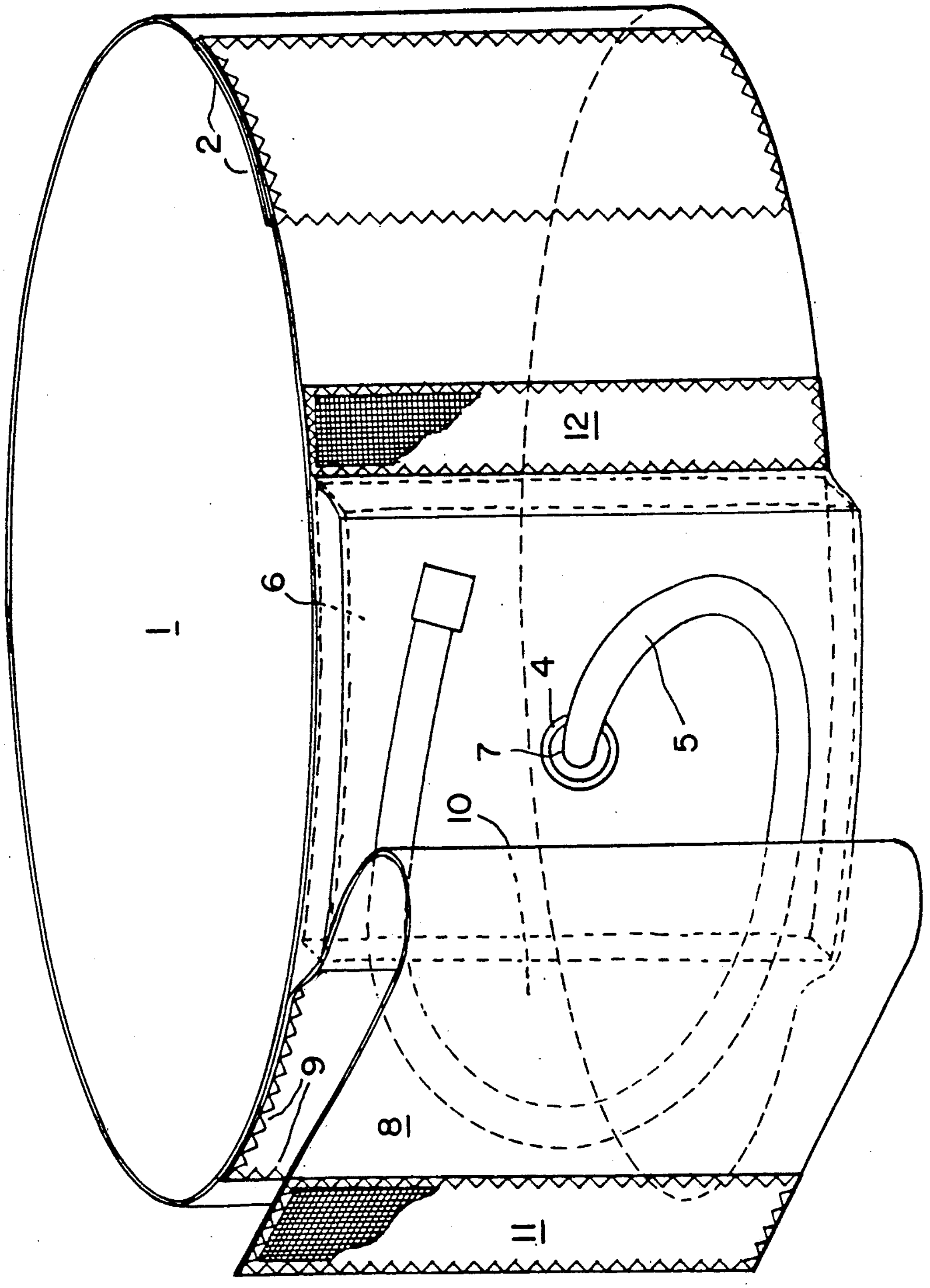
FIG. 2 shows the invention with the pocket flap in an open position exposing the hole through which the gastrostomy tube protrudes.

Referring to FIG. 2 of the drawings, a hole (4) through the main body (1) of the invention allows the gastrostomy tube (5) to project through. Inside the main body (1) of the invention, between the two layers of fabric is positioned a square foam pad (6) approximately ½" to 1" thick. Said foam pad (6) is centered on the hole (4) through the main body (1) of the invention, and itself has a hole (7) that corresponds to the hole (4) through said main body (1). Said foam pad (6) is the same width as the main body (1) of the invention. Its function is to help protect the sensitive stomach area of the wearer at the place where the gastrostomy tube (5) projects through the stomach, and provides a bending place for said gastrostomy tube (5) that is slightly away from the stomach.

The pocket flap (8) is constructed in the same manner and of the same material as the main body (1) of the invention (a double layer of cotton-polyester fabric) and is attached with stitches (9) (refer also to FIG. 1) to the main body (1) in such a way that a pocket (10) is formed.

Still referring to FIG. 2, the invention is shown with the loose ends (2) fastened as they would be if the invention were in place around the waist of a wearer. The pocket flap (8) is shown in an open position. At the loose end of the pocket flap (8) is sewn a strip of fastening material (11) such as Velcro® that enables the pocket flap (8) to be sealed in a closed position when attached to a corresponding strip of fastening material (12) that has been sewn to the main body (1) of the invention. The gastrostomy tube (5) is positioned in the pocket (10) of the invention, and when the pocket flap (8) is in a closed position (refer to FIG. 3), said gastrostomy tube (5) is held securely in place.

The length (circumference) of the invention is determined by the waist size of the prospective wearer: the invention is manufactured in several different sizes in order to fit all prospective wearers. The width of the invention is proportional to the length in the approximate ratio as shown in the drawings.

Figure 3:
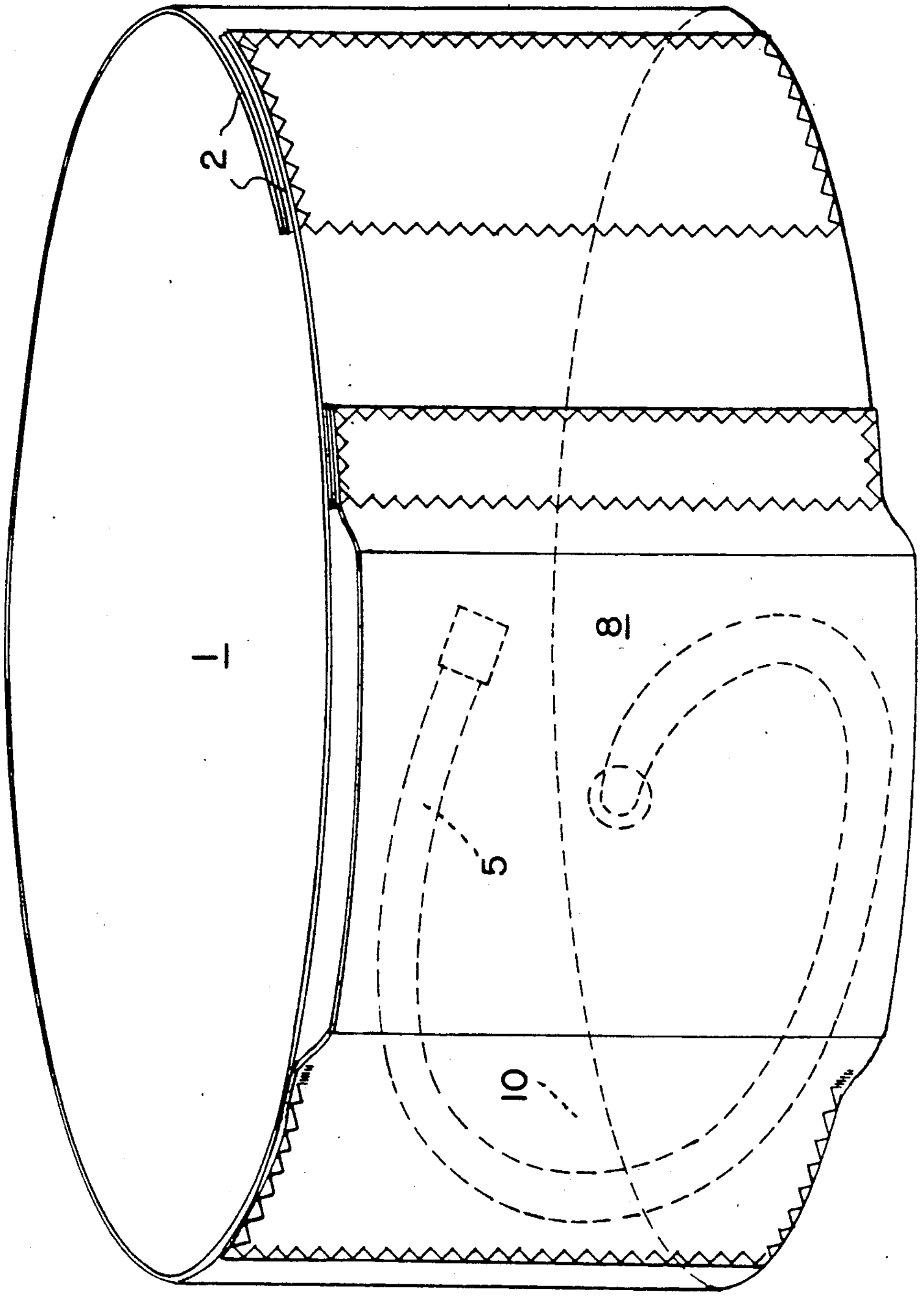
FIG. 3 is a view of the invention as it would appear in use around the waist of a wearer with the pocket flap in a closed position, and with the gastrostomy tube secured inside.

Referring to FIG. 3, the invention is shown as it would appear in use by a wearer. The loose ends (2) of the main body (1) are shown fastened, the pocket flap (8) is shown in a closed position, and the gastrostomy tube (5) is shown secured firmly in place inside the pocket (10) of the invention.

While the invention has been described and illustrated by reference to specific embodiments, this should not be construed as a limitation on the scope of the invention. Many other variations are possible, for example, the invention can be made of other types of fabric or materials than those specified, different methods of fastening the loose ends and the pocket flap are possible (i.e., buckles, snaps, hooks, zippers, etc.), the pocket and pocket flap may be arranged and opened in a different way or direction, different methods of making the invention adjustable for waist size are possible, the foam pad can be of many different materials or possibly even eliminated, etc. Accordingly, the scope of the invention should be determined not by the embodiment illustrated, but by the appended claims and their legal equivalents.

What we claim is:

1. A gastrostomy tube protector and hider comprising a body band of flexible sheet material having opposite ends and means on said opposite ends for releasably securing said ends together, and a hole therethrough intermediate the ends of the waist band a pad of resilient foam fixed to the waist band intermediate the opposite ends thereof, said pad having a hole therethrough overlying and aligned with the hole through the waist band;

a flap of flexible material having one side thereof hingedly connected to the waist band at one side of the pad; and means on an opposite side of the flap and on the waist band at an opposite side of the pad to releasably secure the opposite side of the flap to the waist band, with the flap overlying the resilient pad.

2. A gastrostomy tube protector and hider as in claim 1, wherein the pad of resilient foam is covered with a layer of sheet material having a hole therethrough aligned with the hole through the waist band and the hole through the pad.

* * * * *